(12) United States Patent
Sun et al.

(10) Patent No.: US 10,363,337 B2
(45) Date of Patent: Jul. 30, 2019

(54) TYPE OF THERMAL CATALYTIC OXIDATION MATERIAL FOR AIR PURIFICATION AND APPARATUS THEREFORE

(71) Applicant: KONINKLIJKE PHILIPS N.V., Eindhoven (NL)

(72) Inventors: Ming Sun, Eindhoven (NL); Weizhong Chen, Eindhoven (NL); Declan Patrick Kelly, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 141 days.

(21) Appl. No.: 15/538,418

(22) PCT Filed: Dec. 22, 2015

(86) PCT No.: PCT/EP2015/080977
§ 371 (c)(1),
(2) Date: Jun. 21, 2017

(87) PCT Pub. No.: WO2016/102567
PCT Pub. Date: Jun. 30, 2016

(65) Prior Publication Data
US 2017/0348454 A1 Dec. 7, 2017

(30) Foreign Application Priority Data
Dec. 24, 2014 (WO) ............... PCT/CN2014/094820
Jan. 28, 2015 (EP) ..................... 15152779

(51) Int. Cl.
A61L 9/00 (2006.01)
B01D 53/02 (2006.01)
(Continued)

(52) U.S. Cl.
CPC ............. A61L 9/20 (2013.01); A61L 9/205 (2013.01); B01D 53/86 (2013.01); B01J 23/745 (2013.01);
(Continued)

(58) Field of Classification Search
CPC . B01D 46/0086; B01D 53/00; F24F 11/0017; A61L 9/00
(Continued)

(56) References Cited

U.S. PATENT DOCUMENTS 5,221,520 A 6/1993 Cornwell
2006/0024217 A1 2/2006 Law
2009/0010801 A1 1/2009 Murphy

FOREIGN PATENT DOCUMENTS

DE 19800294 A1 7/1999
DE 10357337 A1 3/2005
(Continued)

OTHER PUBLICATIONS

Venjakob Brochure.
(Continued)

Primary Examiner — Monzer R Chorbaji

(57) ABSTRACT

The invention provides an air purifier (1) comprising a catalytic converter (100), the catalytic converter (100) comprising (i) a catalytically active material (120) and (ii) a heatable material (130) in thermal contact with said catalytically active material (120), wherein the heatable material (130) is heatable by one or more of an alternating electrical field and an alternating magnetic field, the air purifier (1) further comprising a field generator (140), configured free from electrical contact with the heatable material (130) and configured to heat during operation of the air purifier (1) the heatable material (130) by one or more of the alternating electrical field and the alternating magnetic field.

13 Claims, 5 Drawing Sheets

(51) Int. Cl.
*A61L 9/20* (2006.01)
*B01D 53/86* (2006.01)
*B01J 35/00* (2006.01)
*B01J 37/04* (2006.01)
*B01J 23/889* (2006.01)
*B01J 23/745* (2006.01)
*B01J 29/00* (2006.01)

(52) U.S. Cl.
CPC ........... *B01J 23/8892* (2013.01); *B01J 29/00* (2013.01); *B01J 35/002* (2013.01); *B01J 35/0033* (2013.01); *B01J 37/04* (2013.01); *B01D 2257/106* (2013.01); *B01D 2257/404* (2013.01); *B01D 2257/708* (2013.01)

(58) Field of Classification Search
USPC ...... 422/1, 4, 120, 306; 96/108, 223; 55/522
See application file for complete search history.

(56) References Cited

FOREIGN PATENT DOCUMENTS

| | | | |
|---|---|---|---|
| EP | 1201292 A1 | 5/2002 | |
| JP | 2000104946 A | 4/2000 | |
| WO | 03092748 A1 | 11/2003 | |
| WO | WO-03092748 A1 * | 11/2003 | ............... A61L 9/00 |
| WO | 2004112958 A1 | 12/2004 | |
| WO | 2013010328 A1 | 1/2013 | |

OTHER PUBLICATIONS

ODOCAT-H200 Brochure, Doc./Rev #A4/120327.
Innovative Labs Testing Brochure, 2012.
Alan Uraz and Aneliese Ramsay, "Air Purification: Dual Filtration Approach Meets Formaldehyde Challenge—Filtration + Separation", Apr. 12, 2013.

* cited by examiner

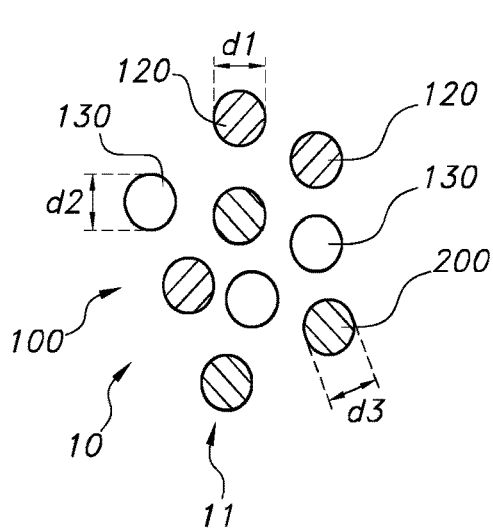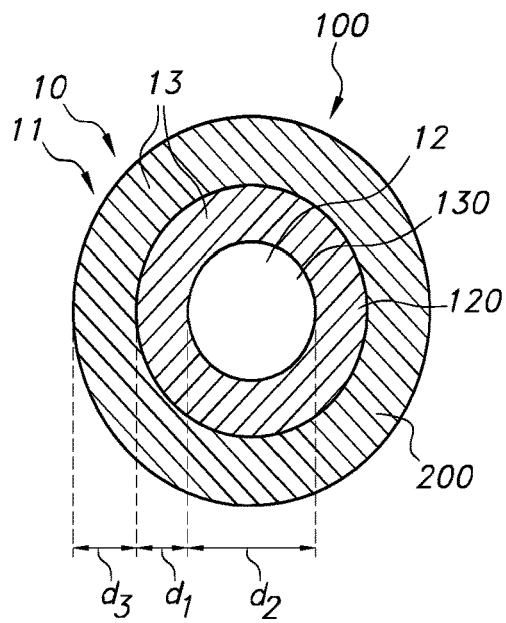
FIG. 2A  FIG. 2B
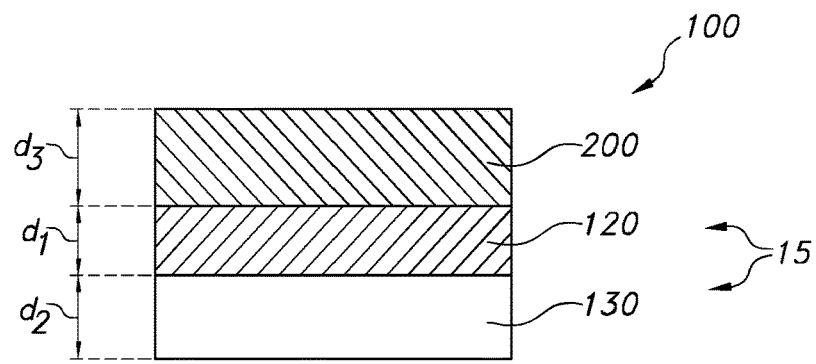
FIG. 2C
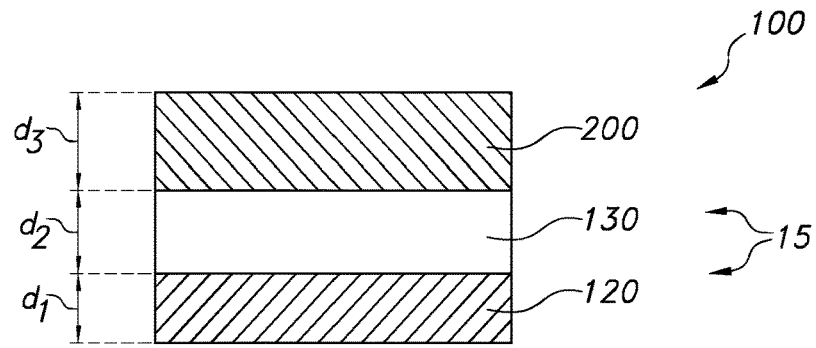
FIG. 2D

TYPE OF THERMAL CATALYTIC OXIDATION MATERIAL FOR AIR PURIFICATION AND APPARATUS THEREFORE

This application is the U.S. National Phase application under 35 U.S.C. § 371 of International Application No. PCT/EP2015/080977, filed on Dec. 22, 2015, which claims the benefit of International Application No. PCT/CN2014/094820 filed on Dec. 24, 2014 and International Application No. 15152779.3 filed on Jan. 28, 2015. These applications are hereby incorporated by reference herein.

FIELD OF THE INVENTION

The invention relates to an air purifier and to a catalytic converter for use with such air purifier. The invention also relates to a method for the abatement of a convertible compound, such as a VOC (volatile organic compound), in air.

BACKGROUND OF THE INVENTION

Air purification systems are known in the art. WO2004/112958, for instance, describes a gold/titanium dioxide photo catalytic/thermocatalytic coating which simultaneously oxidizes volatile organic compounds and carbon monoxide that adsorb onto the coating, into water, carbon dioxide, and other substances. The gold has a size less than 3 nanometers. When photons of the ultraviolet light are absorbed by the gold/titanium dioxide coating, reactive hydroxyl radicals are formed. When a contaminant is adsorbed onto the gold/titanium dioxide coating, the hydroxyl radical oxidizes the contaminant to produce water, carbon dioxide, and other substances. Gold is an oxidation catalyst that lowers the barrier energy of carbon monoxide to oxide the carbon monoxide to carbon dioxide. Therefore, the gold/titanium dioxide coating can also simultaneously oxidize carbon monoxide to carbon dioxide.

SUMMARY OF THE INVENTION

People spend about 80-90% of their time indoors, and indoor environment has important effects on human health and work efficiency. Indoor air is e.g. defined as the air in non-industrial areas of dwellings, offices, schools, shopping center, hospitals and cars, aircraft cabins, submarines cabins etc. Indoor air typically contains a greater number of volatile organic compounds (VOCs, e.g. formaldehyde, benzene, toluene, xylene) at higher concentrations than outdoor air. According to the definition of the World Health Organization (WHO), VOCs are referred as all organic compounds in the boiling point range of 50-260° C., in which aromatics, aldehydes, and halocarbons are the most occurring compounds. VOCs are the major incentive of sick building syndrome (SBS), which are irritation of mucous membranes of eye, nose, throat, and central nervous system (CNS) related. Many VOCs are also known to be toxic and considered to be carcinogenic, mutagenic, or teratogenic. How to eliminate the continuous released VOCs, and prevent their accumulation is important for human health.

Common methods of eliminating VOCs include increasing the air exchange rate and using air purifiers. At present, the use of air purifiers becomes more popular for enclosed indoor air environments. Traditional air purifiers use sorption materials (e.g., granular activated carbon) to adsorb VOCs. However, these techniques only transfer the contaminants to another phase rather than eliminating them. The absorption/saturation lifetime of activated carbon is about 3 months/kg. An additional disposal/handling steps are subsequently required for regeneration and preventing the secondary contamination. Besides, the sorption capacity of carbon decreases significantly for organic compounds with low molecular weight (MW <50-60 gram/mol, fewer than four atoms) and low boiling points (<0° C.).

An alternative remediation technology, which owns a number of advantages over conventional sorption technologies, is the use of thermal catalytic oxidation (TCO). Thermal catalytic oxidation (TCO) is one of the most effective technologies for VOC abatement, because VOCs can be oxidized to $CO_2$ over certain catalysts at much lower temperatures and are expected to have a longer effective life than various adsorption methods. Now, some commercial TCO based air purifiers have been available in the market. These products claim that they can remove formaldehyde under room temperature.

There are several problems for the current TCO materials. Currently, most TCO materials (e.g. $MnO_x$, $CeO_2$, $CoO_x$, $FeO_x$) need to be heated to a certain temperature to increase their catalytic performance. For traditional heating methods, electrical resistance heating wires are the commonly used heating sources. In air purifiers, we need to consider the fire safety. Hence, complex designs are needed to ensure the air can flow through the device and the heat can be safely transferred to the TCO catalyst layer. Under this condition, the environmental air will be heated up unavoidably, which is energy waste, dangerous and uncomfortable for indoor air purification. Further, most TCO materials are solid particles, with low surface area (~1-50 $m^2/g$), which is difficult to capture and catalyze the pollutant gases in air stream. Also lifetime may be an issue. Most TCO catalysts gradually lose activity during use. One effective way to regain the activity is to regenerate the catalyst under high temperature. Conventional heating method will result in various hazards such as fire, release of harmful gases.

Hence, it is an aspect of the invention to provide an alternative air purifier, which preferably further at least partly obviates one or more of above-described drawbacks. Further, it is an aspect of the invention to provide an alternative catalytic converter, which preferably further at least partly obviates one or more of above-described drawbacks. Yet, it is an aspect of the invention to provide an alternative air purification method, which preferably further at least partly obviates one or more of above-described drawbacks.

Hence, in a first aspect the invention provides an air purifier (herein also indicated as "purifier" or "device") comprising (a) a catalytic converter, the catalytic converter comprising (i) a catalytically active material (herein also indicated as "catalytic material") and (ii) a heatable material in thermal contact with said catalytically active material, wherein the heatable material is heatable by one or more of an alternating electrical field and an alternating magnetic field, the air purifier further comprising (b) a field generator, especially configured free from electrical contact with the heatable material, and configured to heat during operation of the air purifier the heatable material by one or more of the alternating electrical field and the alternating magnetic field.

In yet a further aspect, the invention also provides the catalytic converter per se, i.e. a catalytic converter comprising (i) a catalytically active material and (ii) a heatable material in thermal contact with said catalytically active material, wherein the heatable material is heatable by one or more of an alternating electrical field and an alternating magnetic field.

With such air purifier and/or with such catalytic converter, volatile organic compounds and/or other compounds such as $NO_x$ and/or CO may be abated (e.g. by decomposition and/or conversion) with relative low energy input, and in a relative save way. The heatable material is in thermal contact with the catalytically active material and can in this way in a very efficient way provide thermal energy to the catalyst material. Hence, thermal management may be excellent and waste of energy may be minimized. In this way, also risks in terms of handling of the purifier may be minimized as there may be no unnecessary superfluous generation of thermal energy, leading to hot spots that may be dangerous for the use and/or may lead to a shorter lifetime of the purifier than necessary.

An element of the invention comprises the catalytic converter, which may be comprised by the air purifier as defined herein. This catalytic converter may be a particulate material. However, the catalytic converter may also be a solid structure, such as a wire coated with the catalytically active material and/or other materials. The catalytic converter may also include a layered structure. Further, the catalytic converter may include a substrate including the functional materials (such as the catalytically active material and the heatable material and optionally the porous material (see also below)). However, the catalytic converter may also be a monolithic element comprising the functional materials. The catalytic converter may also include a hybrid structure of one of the afore-mentioned embodiments. Some embodiments of the catalytic converter are elucidated below in more detail.

The catalytically active material (one of the functional materials) especially comprises a catalyst configured for catalytic oxidation and/or decomposition of an organic compound, especially a volatile organic compound, and/or for oxidation and/or decomposition of another species that may be available in air, such as one or more of $NO_x$ (i.e. $NO_2$, NO, $N_2O$, etc.), CO, and ozone ($O_3$), especially $NO_x$ and/or ozone. Hence, in an embodiment the catalytically active material comprises a thermal catalytic oxidizing material and/or a thermal catalytic decomposition material. Further, in an embodiment the catalytic converter may (thus) comprise a thermal catalytic oxidizer. The thermal energy is especially used to increase the reaction speed of the catalytic decomposition and/or catalytic oxidation. The use of thermal energy induced by the field generator, see further also below, does not exclude the use of also a source of radiation, to (further) stimulate the catalytic process, for instance by providing one or more of UV, visible and IR radiation to the catalytically active material.

Catalytic active species that may be comprised by the catalytically active material may e.g. be selected from a metal and a metal oxide, as known in the art. Such catalytically active material may optionally essentially consist of such catalytic active species but may in other embodiments e.g. comprise a support, such as a porous material (see also below), comprising such metal and/or metal oxide. The catalytic active species may e.g. include one or more of the elements Pt, Pd, Rh, Ir, Rh, Ag, Au, Co, Mn, Fe, Cu, Ni, Ti, Zr, La, Cr, Nd, Mo, W, Sn, Zn, Cr, Ru, Y, La, Ce, Pr, Nd, Sm, Eu, Gd, Tb, Er, Ho, Dy, Tm, Yb, and Lu. Alternatively or additionally, the catalytic active species may e.g. include one or more alloys of two or more of such elements. Yet alternatively or additionally, the catalytic active species may e.g. include an oxide of one or more of such elements (such as $Fe_2O_3$, MnO, etc.). Herein, terms like "catalitic active species" or "oxide", etc., may also refer to a combination of different catalytic active species and a combination of different oxides (including also mixed oxides), respectively. Examples of suitable catalyst may include one or more of e.g. $MnO_x$ (with especially x=1-3.5), $CeO_2$, $CoO_x$ (with especially x=1-1.33), $FeO_x$ (with especially x=1.33-1.5), Ag, etc. The term "$MnO_x$" may amongst others refer to one or more of $MnO_2$, MnO, $Mn^{4+}_{(1-x)}Mn^{2+}_xO_{(2-x)}(OH)_{2x}$, where x=about 0.06 to about 0.07, and $KMn^{4+}_6Mn^{2+}_2O_{16}$. However, as indicated above, also other catalytic active species may be applied.

The heatable material (another one of the functional materials), herein also indicated as "heat generation material", may e.g. comprise one or more of an iron comprising material, e.g. powder, particle, fiber, wire, and a magnetic material, e.g. $Fe_2O_3$, $Fe_2MnO_4$, $Fe_2CoO_4$, etc. Especially, the heatable may be any solid material that generates heat when being subjected to an alternating electrical field and/or an alternating magnetic field. Magnetic materials that can be used to heat are for instance also known in the magnetic hyperthermia applications. The phrase "configured free from electrical contact with the heatable material" especially indicates that the heating of the heatable material is not done in a conventional way by guiding electricity through an electrically conductive material in a closed circuit. Here, in the present invention, there may be no physical contact between the field generator and the heatable material. Further, the heatable material may optionally be configured in electrical isolation from any electrical circuit.

An example of a suitable electrical field generator includes e.g. an induction coil with in operation an alternating electric current. In principle, the frequency of alternating electrical field can be tuned from 20 kHz to 40 kHz. The voltages can be designed as normal electric appliances like e.g. in the range of 100-240 V. An example of a suitable magnetic field generator may include a copper coil (e.g. with a diameter 16 mm), which in operation produces an alternating magnetic field in the frequency range 300 kHz-1.1 MHz and with an amplitude of up to e.g. 27 kA/m. The magnetic field strength can e.g. be tuned from 5 A/m to 40 kA/m, the frequency can be tuned from 60 Hz to 1.2 MHz.

Further, also a porous material (as third functional material, which is optional) may be applied.

Hence, in an embodiment the air purifier, especially the catalytic converter, may further comprise a porous material, wherein the porous material may especially comprises said catalytically active material. In yet another embodiment, the porous material may further comprise said heatable material. The porous material may include a porous version of one or more of the catalytically active material and the heatable material.

However, the porous material may also be another material having porosity, wherein the porous material may optionally further comprises one or more of said catalytically active material and said heatable material. The porous material may be one or more of macro porous, meso porous, or microporous. Especially porous materials such as one or more of porous alumina and/or porous silica may be applied. Alternatively or additionally a zeolite may be applied. However, also other types of e.g. Al—Si or Al—P systems having porosity may be applied. Non-limiting examples of zeolites that may be used may be selected from the group of ZSM-5, zeolite Y, zeolite Beta. Alternatively or additionally, mordenite may be applied. For instance, porous absorbent material such as e.g. zeolite, metal-organic frameworks (MOF), meso porous silica, activated carbon, etc. may be applied. The term "porous material" may optionally also refer to a plurality of porous materials. When the porous material comprises one or more of the catalytically active material and the heatable material, such functional materials may be within the pores of the porous materials and/or on the pores of the porous materials. Methods to introduce functional materials into pores arc known in the art and include e.g. one or more of incipient wetness and exchange methods.

Hence, e.g. iron materials and magnetic materials can generate and confine the heat within a space down to even nanoscale, and transfer the heat to TCO catalysts. The porous material can capture and concentrate (organic) pollutant gases (e.g. VOCs) from the air (stream), which will increase the contacting and reaction time with TCO catalyst. The TCO catalyst can decompose (organic) pollutant compounds (e.g. VOCs) into e.g. $CO_2$ and $H_2O$ at elevated temperature. Hence, in a specific embodiment the catalytically active material is configured to abate volatile organic compounds (VOCs). In yet a further embodiment, the catalytically active material is configured to abate one or more of (i) volatile organic compounds (VOCs), (ii) ozone ($O_3$), (iii) $NO_x$, and (iv) particulate material (such as ultra fine particles) in air. Alternatively or additionally, the catalytically active material is configured to abate CO (such as by oxidation into $CO_2$). Iron materials and magnetic materials can generate heat by an externally generated alternating induction field and magnetic field, respectively. The size and shape of iron materials and magnetic materials can be tuned as requirements. By using e.g. nano sized materials, the heating space can be confined down to nanoscale. The heat will be transferred to each contacted TCO catalyst unit directly and consumed with high efficiency. The heat will not substantially diffuse into the environment, which is energy saving and enhances safety. Porous materials may possess a large surface area (e.g. >300 $m^2/g$) and tunable pore sizes (such as e.g. 0.3 nm-50 nm), which can capture and concentrate various VOCs (e.g. diameter: formaldehyde ~0.45 nm, benzene ~0.58 nm, toluene ~0.6 nm, xylene ~0.63-0.69 nm). By contacting porous materials with TCO catalysts, the captured VOCs molecules will diffuse onto the surface of TCO catalysts, which will be decomposed at certain temperatures. Further, the intermediate TCO products can be resorbed by porous/absorption materials, and decomposed completely by releasing and decomposition circulation. The synergistic effects of porous materials and TCO catalyst may enhance their lifetime and elongate their lifetime. Likewise this may apply to catalysts other than TCO catalysts.

As indicated above, some embodiments of the catalytic converter are elucidated in more detail.

In an embodiment the air purifier, especially the catalytic converter, may comprise particulate material, wherein the particulate material comprises a mixture of catalytically active material and heatable material. This embodiment may include different variants, such as particulate material having different particles, with each subset of particles comprising one of the functional materials, with thus at least two subsets of particulate materials (the catalytic (particulate) material and the heatable (particulate) material). However, the embodiment may also include a variant wherein two or more of the functional materials have been combined and processed into hybrid particles including two or more functional materials (and thus having two or more functionalities). Hence, in an embodiment the particulate material comprises particles including at least the catalytically active material and the heatable material. In yet a specific embodiment, the particulate material comprises particles including a core comprising said heatable material and a shell comprising said catalytically active material. In yet a further embodiment, the particulate material further comprises a porous material. This porous material may be provided as separate particles. However, this porous material may also be provided as shell or layer on a heatable material core. Alternatively or additionally, it may be provided as shell or layer on a catalytically active material layer or shell (or optionally core). Yet in another variant, it may be provided as shell or layer on a heatable material core, with the catalytically active material comprised by the porous material (layer or shell).

Hence, a plurality of different embodiments is possible, which are amongst others listed above, without being exhaustive. In further general embodiments, which may be combinable with amongst others the above described embodiments, one or more of the catalytically active material and the heatable material are independently configured as one or more of (i) particulate material, (ii) a layer, and (iii) a wire, and wherein independently the one or more of (i) the particulate material, (ii) the layer, and (iii) the wire have at least one dimension of 50 μm or less, e.g. in the range of 5 nm to 50 μm, such as 10 nm to 40 μm. The phrase "are independently configured" indicate that either the catalytically active material or the heatable material or both materials are configured as further describe herein. Further, the phrase "configured as one or more" indicates that a catalytic converter may be provided wherein e.g. the catalytically active material may be provided as particles and/or as layer. Further, the conditions with respect to one or more dimensions may relate to only the particles or only the layer or both the particles and the layer.

Hence, the above embodiments include e.g. a thick (>50 μm) or thin (≤50 μm) layer of heatable material with thereon large (>50 μm) or small (≤50 μm) particles, but with at least one of these dimensions 50 μm or less. The term "dimension" may especially relate to length, width, height, and diameter. For instance, a layer may be provided with a height of 50 μm. Note that with the present invention also much smaller dimensions may be included. For instance, the heatable material may include particulate heatable material having particle dimensions in the range of 10 μm or smaller, such as 1 μm or smaller, or even 100 nm or smaller, i.e. in the nanometer size domain. Likewise, this may apply to layers or particles or wires (essentially) comprising catalytically active material. The term "wire" may also include fiber.

In a further specific embodiment, the catalytic converter comprises a layered structure, comprising at least a layer comprising said catalytically active material and a layer comprising said heatable material. Optionally, one or both of these layers may be porous. In yet a further embodiment, there may be a porous layer in between these functional layers. In general, such intermediate layer will be thin, such as <10 μm, like <5 μm, especially <1 μm, or even smaller, such as <0.1 μm, in order to remain thermal contact.

For good thermal contact, it may especially be beneficial when the functional materials are in physical contact with each other. Hence, in yet a further specific embodiment, the heatable material is configured in physical contact with said catalytically active material. When the heatable material and the catalytically active material are not in physical contact with each other, especially the distance between these materials is small, such as <10 μm, like <5 μm, such as <1 μm, or even smaller, such as <0.1 μm, and/or there may be a thermally conductive material arranged between the heatable material and the catalytically active materials. Hence, in these ways there is also thermal contact heatable material and the catalytically active material.

The air purifier may be applied in different ways. For instance, it may be integrated in an existing ventilation system or an existing air conditioning systems, etc. Hence, in such applications the air purifier does not need a gas flow generator, integrated with the air purifier, as in such embodiment an external gas flow generator may be used. However, alternatively or additionally, in an embodiment the air purifier may further comprise a gas flow generator configured to bring air in contact with the catalytically active material. A gas flow generator may include one or more of a pump, a fan, or other ways like through a chimney effect, etc. Further, the "gas flow" and "gas flow generator", are especially an air flow and air flow generator, respectively.

In yet a further embodiment, the air purifier may further comprising a sensor especially configured to sense a molecule in air, and a control unit, wherein the control unit is configured to control the field generator as function of a sensor signal of the sensor and a predetermined level of said molecule. The term "molecule" may also relate to a plurality of (different) molecules. Alternatively or additionally, the control unit is configured to control the (optional) gas flow generator as function of a sensor signal of the sensor and a predetermined level of said molecule. Yet alternatively or additionally, the sensor may be configured to measure one or more of temperature, humidity, pressure, a presence of a person (in a space), etc. Also then, the control unit is configured to control one or more of the field generator and the optional gas flow generator as function of a sensor signal of the sensor. The term "sensor" may optionally also refer to a plurality of (different) sensors. Likewise this may apply to the term "sensor signal". In this way, the air purifier may e.g. operate at a lower level or higher level, dependent upon the sensor signal. For instance, when there are more persons in a space and/or when a molecule level is higher than desired, the air purifier may operate at a higher level, i.e. have a higher abatement of oxidizable gaseous molecules. The molecule to be sense in air may e.g. be selected from the group consisting of a VOC, $NO_x$, CO, etc. Alternatively or additionally, the air purifier may further comprise a sensor especially configured to sense a particle in air, such as ultra fine particles. Especially, UFP is defined as (air-borne) particulate matter of nanoscale size, especially less than 100 nanometres in diameter (or equivalent diameter in the case of a non-spherical particle, i.e. the diameter which would be obtained when the particle with the same volume would be a spherical particle).

The term "space" in relation to a location of the air purifier or to the use of the air purification method, may for instance relate to a (part of) hospitality area, such as a restaurant, a hotel, a clinic, or a hospital, etc. The term "space" may also relate to (a part of) an office, a department store, a warehouse, a cinema, a church, a theatre, a library, etc. However, the term "space" also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a control room, a security room, etc.

The air purifier may be configured as device, especially an integrated device. However, the air purifier may also be configured as system or comprised by a system, such as a combination of separate items functionally connected to each other. For instance, the system may comprise an air purifier, especially an (integrated) air purifier device, a gas flow generator, a sensor, and a control unit (configured to control the air purifier device and the gas flow generator, especially as function of a sensor signal of the sensor).

Hence, as indicated above the invention also provides in yet a further aspect the catalytic converter per se.

In yet another aspect, the invention also provides a method for the abatement of a convertible compound in air, the method comprising using the air purifier as defined herein, contacting in a contacting stage said air with the catalytically active material while at least temporarily subjecting the heatable material to one or more of an alternating electrical field and an alternating magnetic field before the contacting stage and/or during at least part of the contacting stage. As indicated above, contacting may be facilitated with a gas flow generator that is integrated in the device and/or a gas flow generator that is (entirely) external from the device. Further, heating of the catalytically active material (via the heatable material) may be done during the contacting stage, or may be done before the contacting stage. In general, during the entire period the device should convert (abate) the undesired species, the alternating field is applied to the heatable material. During the contacting stage the undesired specie may be abated (e.g. oxidized and/or decomposed) by the catalytically active material which is at elevated temperatures. Especially, the alternating field/the field generator is applied to heat the catalytically active material to a temperature selected from the range of 30-600° C., such as 50-500° C.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 2a-2g schematically depict some aspects of the catalytic converter;

The schematic drawings are not necessarily on scale.

DETAILED DESCRIPTION OF THE EMBODIMENTS

Figure 1A:
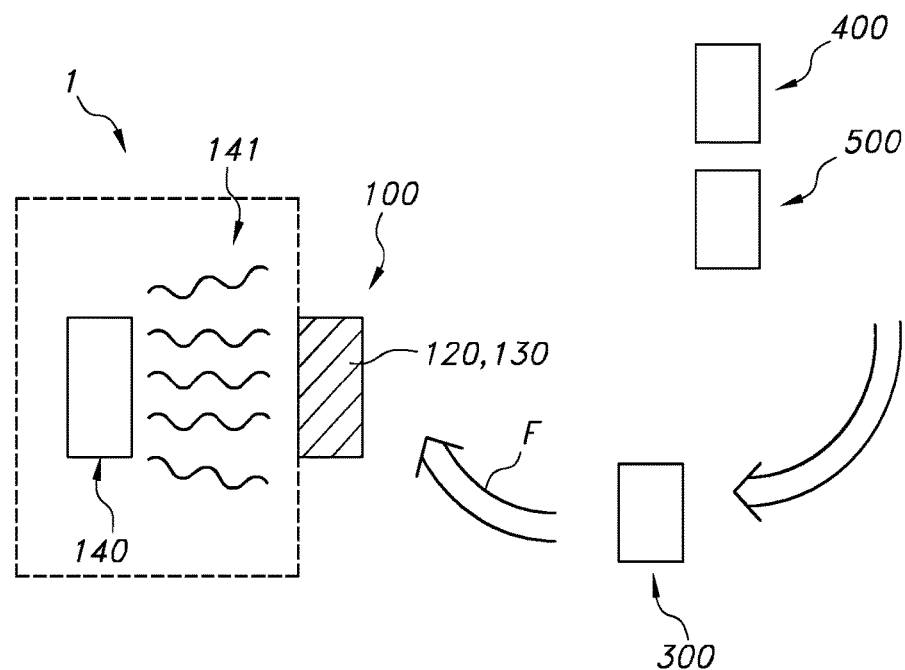
FIGS. 1a-1b schematically depict some aspects of the air purifier.
Figure 1B:
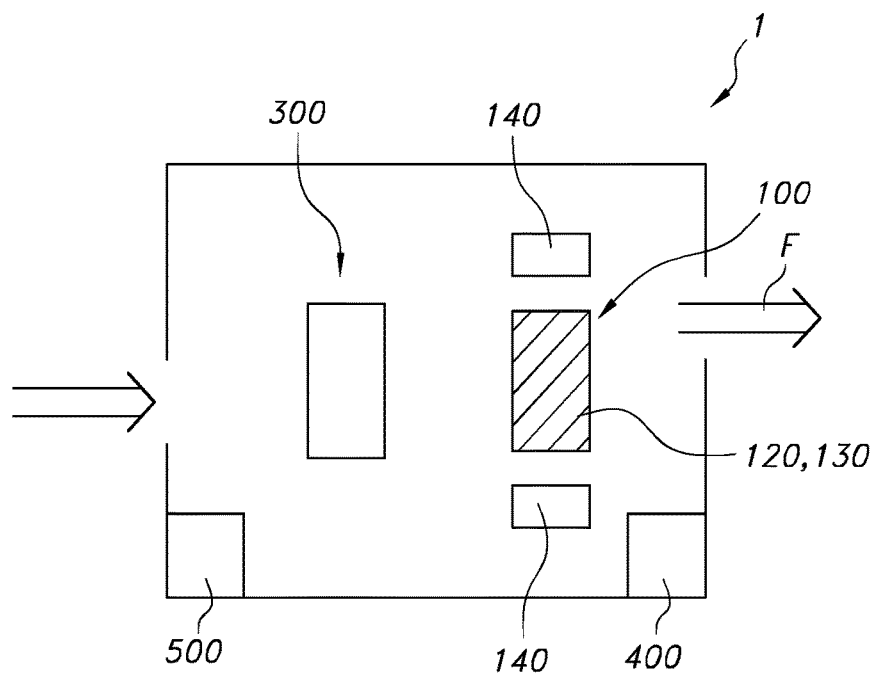

FIGS. 1a-1b schematically depict embodiments of an air purifier 1 comprising a catalytic converter 100. The catalytic converter 100 comprises a catalytically active material 120 and a heatable material 130 in thermal contact with said catalytically active material 120. Further, the heatable material 130 is heatable by one or more of an alternating electrical field and an alternating magnetic field, indicated with reference 141. The air purifier 1 thereto further comprises a field generator 140, especially configured free from electrical contact with the heatable material 130, but at least configured to heat during operation of the air purifier 1 the heatable material 130 by one or more of the alternating electrical field and the alternating magnetic field 141. Reference F indicates a gas flow (i.e. especially an air flow).

Reference 300 indicates a gas flow generator (configured to generate gas flow F) and references 400 and 500 indicate a sensor and control unit, respectively. These may be integrated in the air purifier or may be configured separate thereof. The air purifier 1 and the sensor 400 and the control unit 500 are especially functionally coupled to each other (e.g. in an integrated device or as system). The dashed line in FIG. 1a may indicate a housing, which may include the field generator and which may at least partly enclose the catalytic converter 100.

FIG. 1b schematically depicts a variant with a gas flow generator 300 included in the air purifier 1. To this end, the air purifier 1 may include a chamber enclosing the gas flow generator 300 and the catalytic converter 100 and the field generator 140.

In this invention, we propose a series of—amongst others—new multi functional TCO materials for air purification. In the new materials, a novel localized heating is realized through material engineering. The material structure design may—amongst others—be based on the material function, size and shape. FIGS. 2a-2g schematically illustrate a number of possible structures of the catalytic converter, without being exhaustive, with reference 120 indicated in the catalytic material, reference 130 indicating the heatable material, and reference 200 indicating the porous material, and with references d1, d2 and d3, indicating a dimension of these functional materials, respectively, especially in these examples their thicknesses. Reference 11 indicates particles and reference 10 indicates particulate material (comprising these particles 11).

In FIG. 2a, a random blending structure is shown. The abovementioned three functional materials may be mixed, and optionally the materials may thereafter be granulated into desired size and shape. Hence, the functional materials may be mixed as particulate materials, and be used as such, or may be further granulated, to provide composite particles. In FIG. 2a, by using commercial products, iron powders (or magnetic iron oxide powders) as heating generation materials (FIG. 4a.), zeolite powders as porous materials (FIG. 4c.), MnO), powders as TCO materials (FIG. 4b.), and mixing them together with stable binders (e.g. bentonite) and granulation into desired particles, and then calcining the granulated particles at high temperature (e.g. 200-500° C.) to activate the porous materials and TCO catalysts.

Also core/shell structures may be provided, see e.g. FIG. 2b, with the core being indicated with reference 12 and the shell(s) being indicated with reference 13. For instance by using heating generation materials as core, TCO catalyst as intermediate shell, and porous materials as outer shell. The core size and shell thickness can be controlled with the accuracy of nanometer, and even with atomic-scale precision (FIG. 2b).

Also heterostructures may be provided, such as sandwich structure, with e.g. a TCO catalyst as intermediate layer, and the heating generation material and porous materials as outer layers. The thickness of each layer can be controlled with the accuracy of nanometer, and even with atomic-scale precision. Two variants are schematically depicted in FIGS. 2c and 2d, with reference 15 indicating a layer.

Figure 2E:
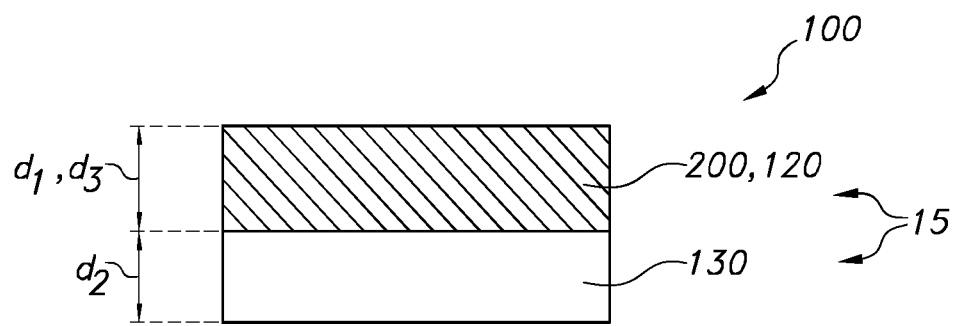
Figure 2F:
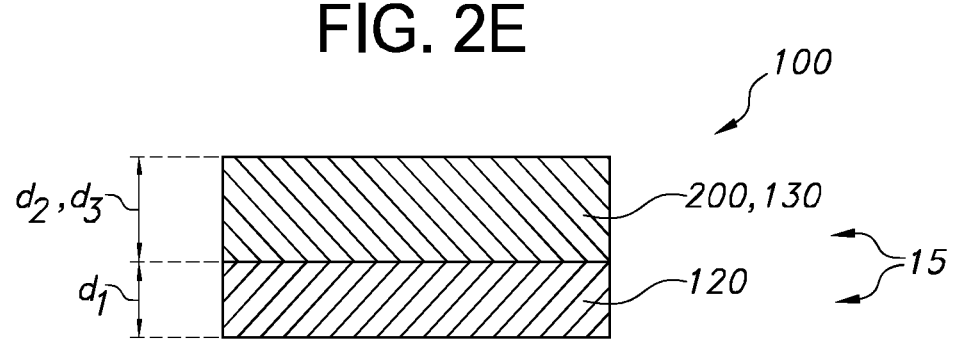

Also hybrids, alloys or heterostructure may be provided, for instance by using porous $MnO_x$ as both porous materials and TCO materials, and then combine with magnetic materials (FIG. 2e) or by using porous $FeO_x$ as both porous materials and magnetic materials, and then combine with TCO materials (FIG. 2f).

In some of the above embodiments, also the porous material 200 is included. As mentioned above, this functional material is optional.

Figure 2G:
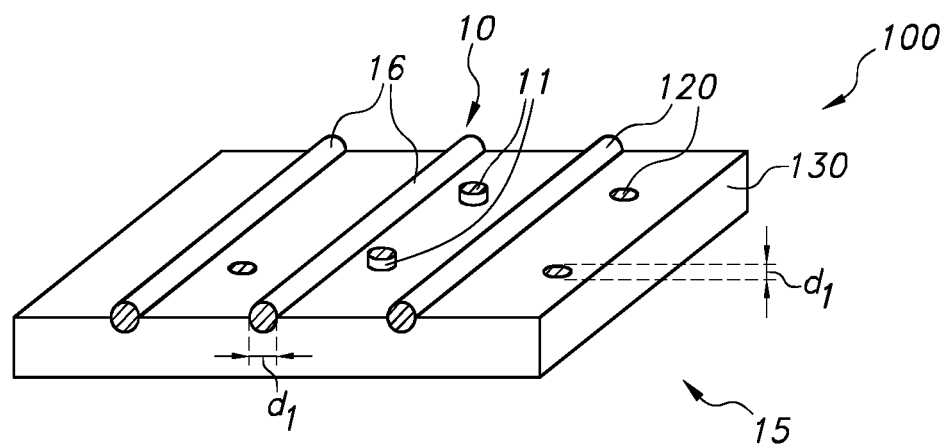

FIG. 2g schematically depicts an embodiment of catalytic converter 100, with a layer 15 of the heatable material 130 and thereon wires 16 and particles 11 comprising the catalytically active material 120.

Figure 3:
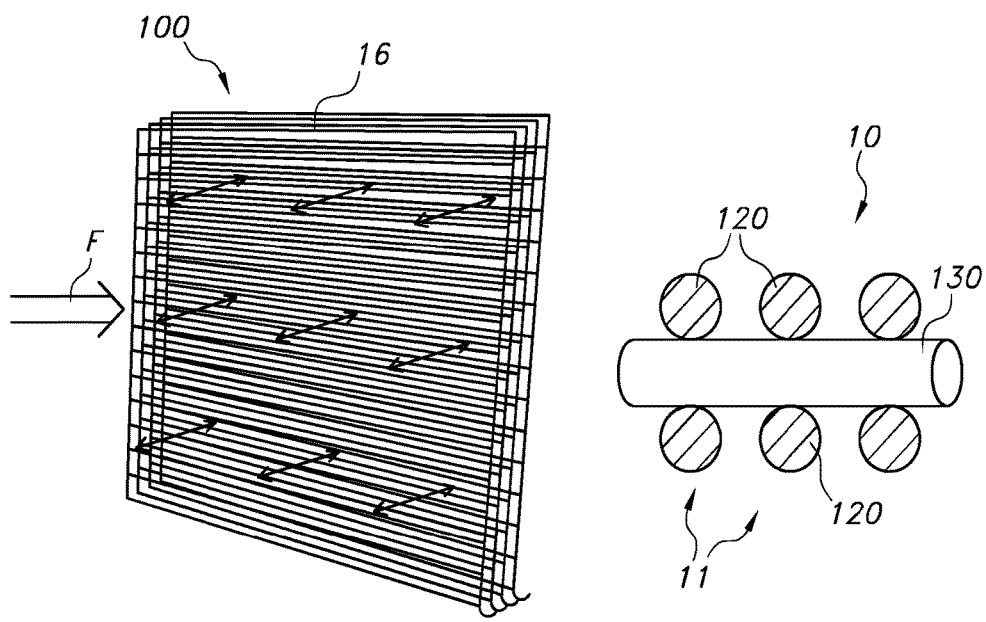
FIG. 3 schematically depicts an embodiment of the air purifier.

FIG. 3 schematically depicts an embodiment of the catalytic converter 100, including an enlargement of part thereof. Thereof catalytic converter 100 comprises a wire gauze comprising the heatable material 130. On the wires 16 of the wire gauze the catalytically active material 120 may be applied as particles 11. Alternatively or additionally, the particles 11 comprises heatable material 130 (see also above). When the heatable material comprises magnetic material, the magnetism may also be used to adhere the particles to an iron or otherwise magnetic support, such as here the wires 16.

Figure 4:
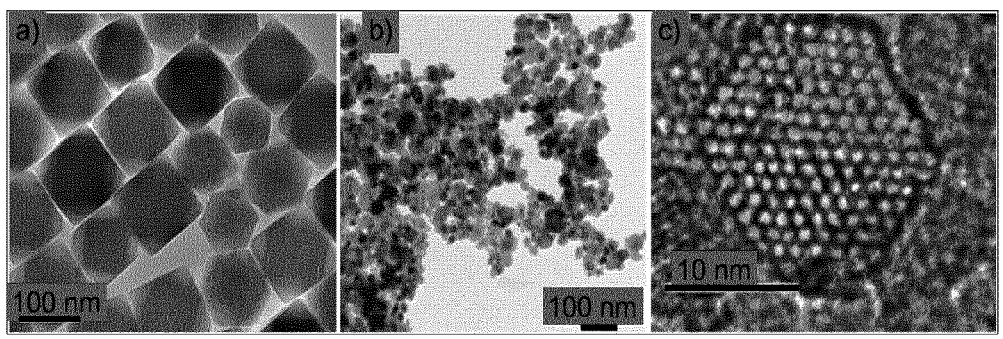
FIG. 4 shows TEM images of (a) magnetic iron oxide nanoparticles (~110 nm), (b) MnO2 nanoparticles (~20-30 nm), (c) EMT-zeolite nanoparticles (~15 nm)

FIG. 4 shows TEM images of (a) magnetic iron oxide nanoparticles (~110 nm), (b) $MnO_2$ nanoparticles (~20-30 nm), (c) EMT-zeolite nanoparticles (~15 nm).

Figure 5:
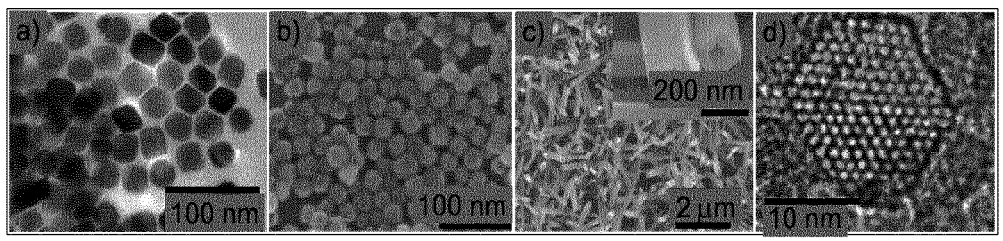
FIG. 5 shows TEM and SEM images of (a) magnetic iron oxide nanoparticles (22 nm), (b) $MnO_2$ nanoparticles (~25 nm), (c) $MnO_2$ nanotubes (diameter: 100 nm, wall thickness: 30 nm, length: several microns), (d) EMT-zeolite nanoparticles(~15 nm)

FIG. 5 shows TEM and SEM images of (a) magnetic iron oxide nanoparticles (22 nm), (b) $MnO_2$ nanoparticles (~25 nm), (c) $MnO_2$ nanotubes (diameter: 100 nm, wall thickness: 30 nm, length: several microns), (d) EMT-zeolite nanoparticles(~15 nm). The heterostructure designs are more flexible, and the synthesis methods are similar to core/shell structure. For example, sandwich structure (FIG. 2c), similar sized magnetic iron oxide nanoparticles (FIG. 5a) and porous zeolite materials (FIG. 5d) can epitaxy growth on the opposite crystal faces of $MnO_2$ nanoparticles (FIG. 5b). By using larger sized $MnO_2$ nanotubes (FIG. 5c), smaller sized magnetic iron oxide nanoparticles (FIG. 5a) and porous zeolite materials (FIG. 5d) can be loaded on the nanotubes surface or filled into nanotubes.

Figure 6:
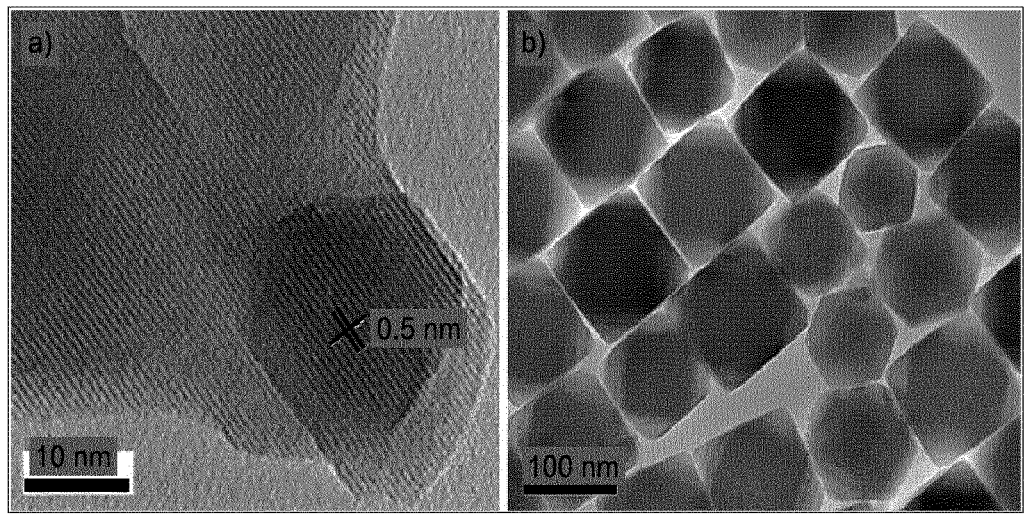
FIG. 6 shows TEM images of (a) porous $MnO_x$ molecular sieve (K-OMS-2), (b) magnetic iron oxide nanoparticles (~110 nm)

FIG. 6 shows TEM images of (a) porous MnOx molecular sieve (K-OMS-2), (b) magnetic iron oxide nanoparticles (~110 nm). In FIG. 2e, for example, by using porous MnOx molecular sieve (K-OMS-2) (FIG. 6a) as both porous materials and TCO materials, and then combine with magnetic iron oxide nanoparticles (FIG. 6b).

Figure 7:
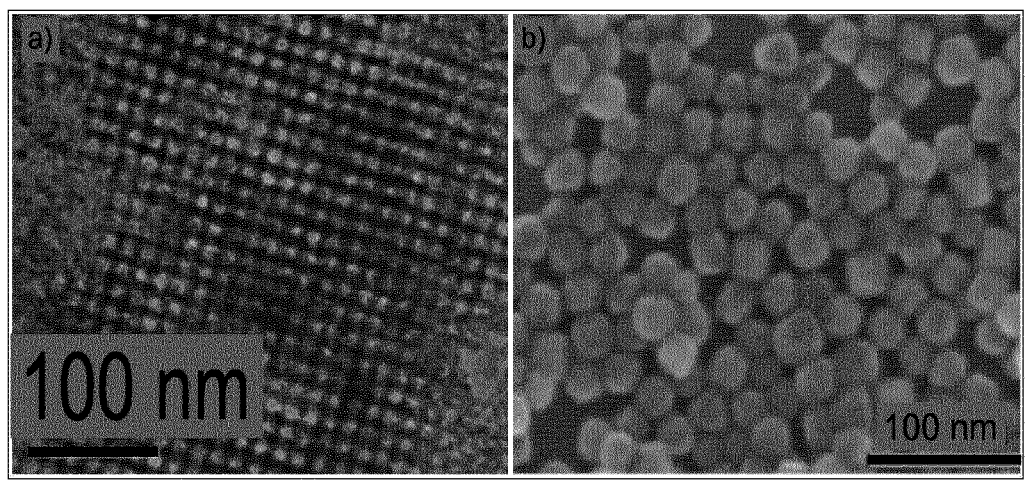
FIG. 7 shows TEM and SEM images of (a) porous magnetic iron oxide nanoparticles (>100 nm), (b) MnO2 nanoparticles (~25 nm).

FIG. 7 shows TEM and SEM images of (a) porous magnetic iron oxide nanoparticles (>100 nm), (b) $MnO_2$ nanoparticles (∞25 nm). In FIG. 2f, for example, by using porous magnetic $Fe_2O_3$ (FIG. 7a) as both porous materials and magnetic materials, and then combine with $MnO_2$ (FIG. 7b) TCO materials.

Hence, herein we propose amongst others new types of multifunctional TCO materials for air purification. The multifunctional TCO materials are the combination and integration of at least two types of functional materials: heat generation materials, catalysts, such as TCO catalysts, and optionally porous materials. The heat generation materials can generate and confine the heat within a space down to nanoscale. The will be transferred to nearly contacted TCO catalyst unit directly and consumed with high efficiently. The heat may substantially not diffuse into the environment, which is energy saving and safety. Porous Material can capture and concentrate organic pollutant gases (e.g. VOCs) from the airstream, which will increase the contacting and reaction time with TCO catalyst. The material structures design are flexible, such as random blending structure, core/shell structure, heterostructure and alloyed structure, which may be based on the material function, size and shape. Parts of structures may be combined with magnetic materials, so they can be absorbed on the iron substrate (e.g. iron mesh) automatically and robustly, which may simplify the coating process significantly.

Above, many examples are described in relation to TCO catalysts. However, in other embodiments equally well other catalysts may be applied, as indicated above.

The invention claimed is:

1. An air purifier comprising:
   a catalytic converter that comprises a multifunctional material, wherein the multifunctional material includes a combination of at least:
   (i) a catalytically active material, and
   (ii) a heatable material, wherein the heatable material is heatable in response to one or more of an alternating electrical field and an alternating magnetic field; and
   a field generator, configured free from electrical contact with the multifunctional material, for generating the one or more of the alternating electric field and the alternating magnetic field during operation of the air purifier, wherein the heatable material is heated by the one or more of the alternating electrical field and the alternating magnetic field,
   wherein one or more of the catalytically active material and the heatable material of the multifunctional material are independently configured as one or more of (i) particulate material, (ii) a layer, and (iii) a wire, and wherein independently the one or more of (i) the particulate material, (ii) the layer, and (iii) the wire have at least one dimension of 50 µm or less.

2. The air purifier according to claim 1, wherein the multifunctional material further comprises a combination of (i) the catalytically active material, (ii) the heatable material and (iii) a porous material.

3. The air purifier according to claim 1, wherein the catalytically active material is configured to abate one or more of (i) volatile organic compounds (VOCs), (ii) ozone ($O_3$), (iii) $NO_x$, and (iv) particulate material in air.

4. The air purifier according to claim 1, wherein the multifunctional material further comprises a particulate material mixture of particles including at least (i) the catalytically active material and (ii) the heatable material.

5. The air purifier according to claim 4, wherein the particulate material mixture further comprises particles having (i) a core that includes said heatable material and (ii) a shell that includes said catalytically active material.

6. The air purifier according to claim 4, wherein the particulate material mixture includes a porous material.

7. The air purifier according to claim 1, wherein the catalytic converter further comprises a layered structure, wherein the layered structure has at least a layer including said catalytically active material and a layer including said heatable material.

8. The air purifier according to claim 1, wherein the heatable material is configured in physical contact with said catalytically active material.

9. The air purifier according to claim 1, further comprising a gas flow generator configured to bring air in contact with the catalytically active material.

10. The air purifier according to claim 1, further comprising a sensor configured to sense a molecule in air, and a control unit, wherein the control unit is configured to control the field generator as a function of (i) a sensor signal of the sensor and (ii) a predetermined level of said molecule.

11. The catalytic converter as defined in claim 1.

12. A method for the abatement of a convertible compound in air, the method comprising using the air purifier according to claim 1, contacting in a contacting stage said air with the catalytically active material while at least temporarily subjecting the heatable material to one or more of an alternating electrical field and an alternating magnetic field before the contacting stage and/or during at least part of the contacting stage.

13. An air purifier as claimed in claim 1, wherein independently the one or more of (i) the particulate material, (ii) the layer, and (iii) the wire have at least one dimension selected from the group consisting of 10 μm or less, and 100 nm or less.

* * * * *